United States Patent
Yu et al.

(10) Patent No.: US 7,477,060 B2
(45) Date of Patent: *Jan. 13, 2009

(54) COATING IMPEDANCE MONITORING SYSTEM

(75) Inventors: Steven Y. Yu, Austin, TX (US); Michael R. Matthews, Austin, TX (US); Gary A. Shreve, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 123 days.

This patent is subject to a terminal disclaimer.

(21) Appl. No.: 11/318,709

(22) Filed: Dec. 27, 2005

(65) Prior Publication Data

US 2007/0144272 A1  Jun. 28, 2007

(51) Int. Cl.
*G01R 27/08* (2006.01)
*G06F 19/00* (2006.01)

(52) U.S. Cl. .......................... 324/693; 702/34; 702/35; 324/700

(58) Field of Classification Search ................. 324/700, 324/699, 693, 691, 649, 600; 702/33, 34, 702/35, 36
See application file for complete search history.

(56) References Cited

U.S. PATENT DOCUMENTS

| | | | |
|---|---|---|---|
| 4,380,763 A | 4/1983 | Peart et al. | |
| 4,780,664 A | 10/1988 | Ansuini et al. | |
| 4,962,360 A | 10/1990 | Homma et al. | |
| 5,195,046 A * | 3/1993 | Gerardi et al. | 702/35 |
| 5,306,414 A | 4/1994 | Glass et al. | |
| 5,310,470 A | 5/1994 | Agarwala et al. | |
| 5,323,429 A | 6/1994 | Roarty et al. | |
| 5,338,432 A | 8/1994 | Agarwala et al. | |
| 5,367,583 A | 11/1994 | Sirkis | |
| 5,746,905 A * | 5/1998 | Murray | 324/699 |
| 5,859,537 A | 1/1999 | Davis et al. | |
| 6,054,038 A | 4/2000 | Davis et al. | |
| 6,063,486 A | 5/2000 | Kobayashi | |
| 6,144,026 A | 11/2000 | Udd et al. | |
| 6,316,646 B1 | 11/2001 | Tacke et al. | |
| 6,328,878 B1 | 12/2001 | Davis et al. | |
| 6,342,295 B1 | 1/2002 | Kobayashi | |
| 6,384,610 B1 | 5/2002 | Wilson | |
| 6,399,939 B1 * | 6/2002 | Sundaresan et al. | 250/231.1 |
| 6,445,565 B1 | 9/2002 | Toyoda et al. | |
| 6,683,463 B2 | 1/2004 | Yang et al. | |
| 6,896,779 B2 | 5/2005 | Thomas, III et al. | |

(Continued)

FOREIGN PATENT DOCUMENTS

EP  1 434 048 A1  6/2004

(Continued)

*Primary Examiner*—Harshad Patel
*Assistant Examiner*—Punam Patel
(74) *Attorney, Agent, or Firm*—Gregg H. Rosenblatt (57) ABSTRACT

A detection system for monitoring an engineered structure includes an array of sensors disposable in a predetermined pattern on the engineered structure and disposable between a surface of the engineered structure and a protective coating substantially covering the surface. The detection system also includes a data acquisition system in communication with the array of sensors for retrieving data from the sensors. The array of sensors can provide data corresponding to at least one of a degree of cure of the protective coating, a health of the cured protective coating, and a corrosion rate of the engineered structure at each of the sensors.

11 Claims, 8 Drawing Sheets

U.S. PATENT DOCUMENTS

| | | |
|---|---|---|
| 6,911,828 B1 | 6/2005 | Brossia et al. |
| 7,244,500 B2 * | 7/2007 | Watts et al. ............ 428/408 |
| 2002/0078752 A1 | 6/2002 | Braunling et al. |
| 2002/0153873 A1 | 10/2002 | Shapiro et al. |
| 2004/0045365 A1 * | 3/2004 | Richardson ............ 73/772 |
| 2004/0189331 A1 | 9/2004 | Girshovich et al. |
| 2005/0006251 A1 | 1/2005 | Thomas, III et al. |
| 2005/0034985 A1 | 2/2005 | Zamanzadeh et al. |
| 2005/0036135 A1 | 2/2005 | Earthman et al. |
| 2005/0082467 A1 * | 4/2005 | Mossman ............ 250/227.16 |
| 2007/0120572 A1 * | 5/2007 | Chen et al. ............ 324/700 |

FOREIGN PATENT DOCUMENTS

| | | |
|---|---|---|
| WO | WO 2004/031738 A1 | 4/2004 |
| WO | WO 2004/031739 A2 | 4/2004 |
| WO | WO 2004/065942 A1 | 8/2004 |

* cited by examiner

COATING IMPEDANCE MONITORING SYSTEM

BACKGROUND OF THE INVENTION

1. Field of the Invention

The present invention is directed to a detection system.

2. Related Art

Sensors capable of detecting corrosion are known, such as is described in U.S. Pat. Nos. 6,384,610; 6,328,878; 6,316,646; 5,859,537; 6,054,038; 6,144,026; 4,380,763; 4,780,664; 4,962,360; 5,323,429; 5,367,583; 6,445,565; and 6,896,779. For example, while some of these conventional approaches utilize "embeddable" corrosion sensors, the conventional technologies often employ rigid printed circuit boards and rigid silicon wafer chips. Limitations of such technology include thickness and fragility—placing rigid circuit boards under thin epoxy or paint coatings can cause disruptions in the coating, and silicon wafer-based sensors are prone to fractures, and do not conform to uneven surfaces.

SUMMARY OF THE INVENTION

According to a first aspect of the present invention, a detection system for monitoring an engineered structure includes an array of sensors disposable in a predetermined pattern on the engineered structure and disposable between a surface of the engineered structure and a protective coating substantially covering the surface. The detection system also includes a data acquisition system in communication with the array of sensors for retrieving data from the sensors. The array of sensors can provide data corresponding to at least one of a degree of cure of the protective coating, a health of the cured protective coating, and a corrosion rate of the engineered structure at each of the sensors.

According to another aspect of the present invention, a method of detecting physical conditions in an engineered structure includes providing a data acquisition circuit that provides an activation signal to initiate data collection from an array of sensors, each of the sensors including a sensing portion. The data acquisition circuit searches for at least a portion of the array sensors and records and saves all searched sensor addresses. Data is retrieved from a first sensor of the searched sensors. The retrieved data is analyzed and stored. The stored data is displayed upon request. The analyzed data corresponds to at least one of a degree of cure of the protective coating, a health of the cured protective coating, and a corrosion rate of the engineered structure at each of the sensors.

The above summary of the present invention is not intended to describe each illustrated embodiment or every implementation of the present invention. The figures and the detailed description that follows more particularly exemplify these embodiments.

BRIEF DESCRIPTION OF THE DRAWINGS

The present invention will be further described with reference to the accompanying drawings, wherein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION OF THE EMBODIMENTS

The present invention is directed to a detection system. In particular, the detection system of the exemplary embodiments is embeddable and can be utilized to detect several key characteristics of a coated surface on an engineered structure. First, the detection system can be utilized to detect the degree of cure of a coating that is applied to the surface of an engineered structure. In addition, the detection system can be utilized to detect the health of the coating after cure, e.g., by detecting the deterioration of the coating (e.g., moisture ingress) when exposed to natural elements. Further, the detection system can be utilized to detect the integrity of the surface of the engineered structure, e.g., by detecting physical conditions that promotes corrosion.

In these exemplary implementations, the detection system can be configured to provide real-time and/or periodic (e.g. per hour, per day, per week) data related to one or more physical conditions of an engineered structure through a data acquisition system. This type of data acquisition system can provide for "condition-based" maintenance for engineered structures, as opposed to "preventive" maintenance, which is currently used. Thus, the detection system of the exemplary embodiments can help maximize the operational life of an engineered structure or object by providing real-time data to better manage the scheduling of repairs or replacements of such objects or structures.

Figure 1:
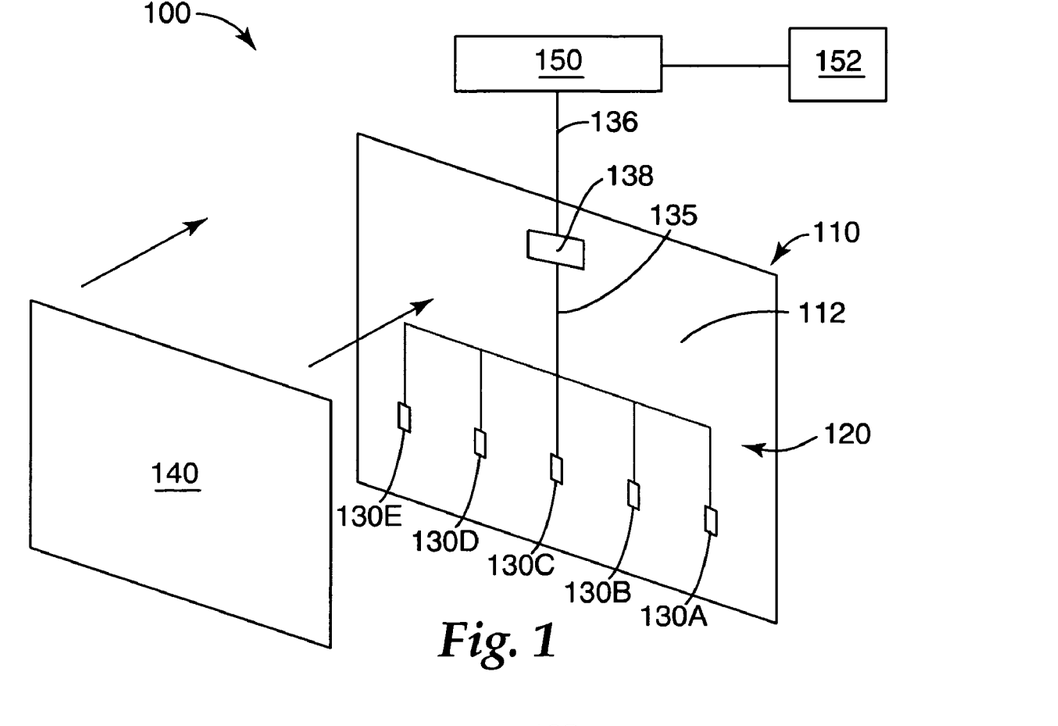
FIG. 1 is an exemplary detection system according to an embodiment of the present invention.

According to an exemplary embodiment of the present invention, FIG. 1 shows a detection system 100 in schematic view. The detection system 100 includes a sensor array 120. In this exemplary embodiment, sensor array 120 includes a plurality of sensors (in this example, a group of five (5) sensors (130A-130E) are shown for simplicity) coupled to a data line or wire connections 135. The sensor array 120 is disposed on a surface 112 of an engineered structure 110. As is explained in further detail below, the embodiments of the present invention can utilize many different types of sensors. For example, in some embodiments, a corrosion sensor configuration having a cathode-anode structure can measure impedance, current, and/or voltage to monitor corrosion. Other types of sensors, such as chemical detectors, can also be utilized.

The sensor array 120 can further include a control circuit or IC 138 that communicates with a data acquisition circuit 150 via a data line 136. In some embodiments, data line 136 can be configured as a multi-line data bus. In accordance with an exemplary embodiment, data acquisition circuit 150 can be remotely located from the particular engineered structure being monitored.

Control circuit or IC 138 can also be coupled to other sensor arrays (not shown) disposed on different areas of the engineered structure 110. For example, the IC 138 can include a network protocol, such as 1-Wire® protocol (Dallas Semiconductor/Maxim Integrated Products, Sunnyvale, Calif., providing a communications structure protocol between sensors and/or sensor groups and the data acquisition circuit. In one exemplary embodiment, IC 138 can include a DS2438 chip, commercially available from Dallas Semiconductor/Maxim Integrated Products (Sunnyvale, Calif.). IC 138 can be dedicated to a single sensor, a group of sensors, or multiple groups of sensors.

Alternatively, as discussed further below, each of the sensors (e.g., 130A-130E) can include IC 138 (or something similar) as part of its structure, making some or all of the sensors uniquely addressable. The control circuit or IC 138 can include one or more address indicators or identifiers that provide the data acquisition circuit 150 with area-specific coating/structure data from area-specific sensor arrays. The data acquisition circuit 150, as is explained in further detail below, can be designed to receive, collate and/or analyze data from the sensors and/or control the sensors with instructions, power, etc.

In an exemplary embodiment, a coating 140 is applied to the surface 112 of the engineered structure 110. The sensors 130A-130E are configured to have a very thin design (e.g., having a sensing portion thickness of about 13 µm to about 75 µm) so that the sensors are easily disposed between the surface 112 and the coating 140. In this manner, the sensors can simultaneously provide data on the health of the coating 140 and the engineered structure 110.

The engineered structure 110 can be any type of structure or object that is exposed to natural elements, such as water, rain, wind, etc. In an exemplary embodiment, the detection system 100 can be utilized in a marine platform (e.g., boat, submarine) to detect the health of the coatings and/or structures within a ballast tank or other structure water-holding structure. As is understood, ballast tanks are used in marine platforms to provide ballast for the vessel. These tanks can be continually filled and/or drained and can also collect debris and other materials. As salt water is a very corrosive substance, periodic and/or real-time coating and/or structure health assessments detected by exemplary detection system 100 can provide critical information related to maintenance planning. According to alternative embodiments, detection system 100 can be used with other types of engineered structures, such as tunnels, bridges, pipes, and aircraft, which are also susceptible to corrosion or other forms of physical deterioration. The physical composition of the structure 110 can be a metal, such as steel, a carbon fiber composite, a ceramic, or a fiberglass based material such as a fiberglass laminate.

To protect structures 110, coating 140 can comprise a coating, such as an epoxy-based coating or paint, such as polyamide epoxies (e.g., an epoxy meeting MIL-spec. 24441) and coating epoxies (e.g., product no. 2216 A/B, available from 3M Company, St. Paul, Minn.). As is explained further below, detection system 100 can be used to detect characteristics such as the cure condition and/or health of coating 140.

Figure 2:
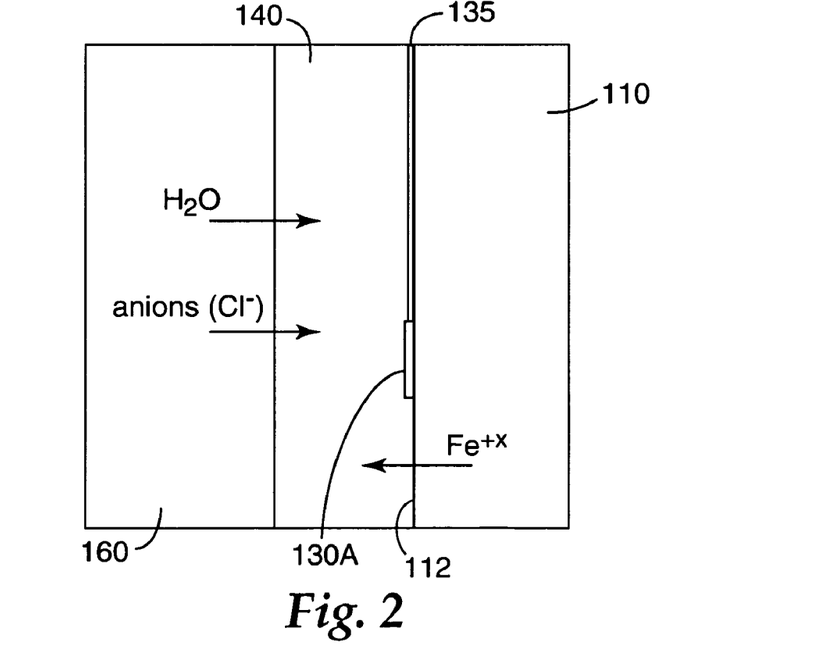
FIG. 2 is a cross-section view of a sensor embedded between a coating and an engineered structure according to an exemplary embodiment of the present invention.

For example, as shown in the cross-section view of FIG. 2, a sensor 130A can be disposed on surface 112 of structure 110, such as a ballast tank. Sensor 130A can be secured to surface 112 via an adhesive, such as a moisture resistant 2-part epoxy (e.g., a Tra-Con 2151 adhesive, available from Tra-Con Corp., Bedford, Mass.), or a double-sided tape or transfer adhesive, such as 3M VHB, available from 3M Company, St. Paul, Minn. Sensor 130A can communicate to the data acquisition circuit via data line 135. Coating 140 is applied to the surface 112 to protect the structure 110 from the corrosive effects of an external substance or material, such as seawater 160. As is explained in more detail below, sensor 130A can detect the health of the coating 140 (e.g. monitoring the impedance by detecting the presence of chemical species, such as chloride), which indicates general coating health as coating 140 deteriorates and as structure 110 starts to corrode.

Figure 3A:
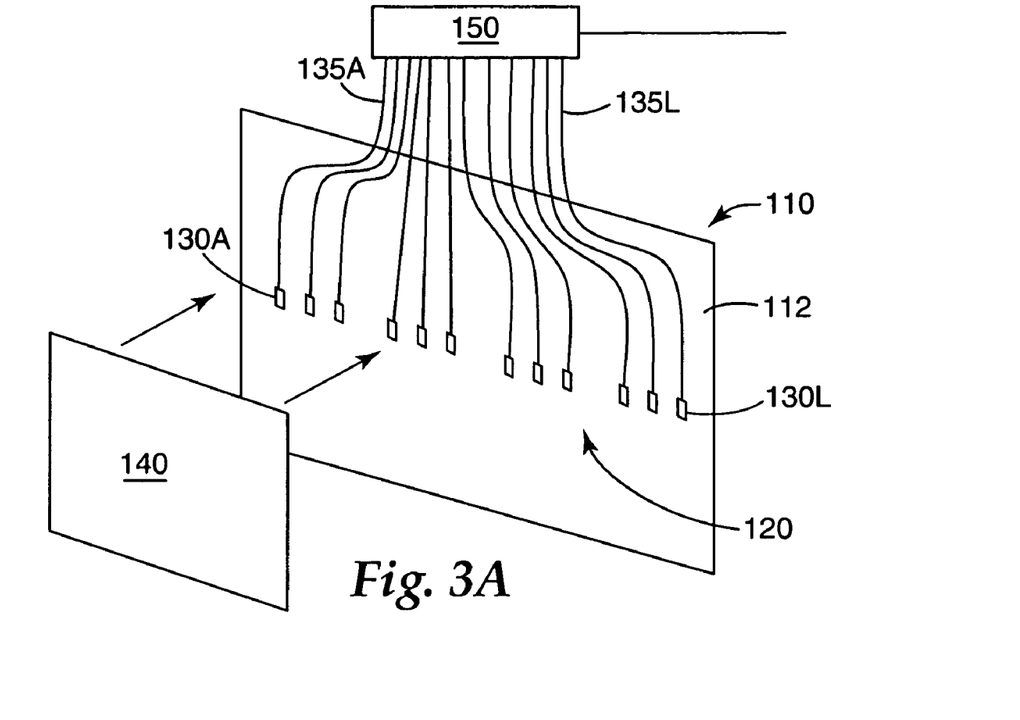
FIG. 3A is an exemplary detection system according to an alternative embodiment of the present invention.

As shown in FIG. 1, sensor array 120 can be configured such that the individual sensors are coupled in parallel to the data acquisition circuit 150. As shown in FIG. 3A, in an alternative embodiment, sensor array 120 can comprise a plurality of individual sensors (in this example, sensors 130A-130L). Here, each individual sensor is coupled directly to the data acquisition circuit 150 (e.g., through data lines 135A-135L). In this embodiment, each sensor can be of simple design and can be coupled to an external voltage and/or current controller located at the data acquisition circuit 150. An external voltage/current controller co-located at the data acquisition circuit, (e.g., a computer controlled potentiostat and frequency response analyzer) can activate each sensor, and read the resulting electrochemical response. This configuration would minimize the complexity of each sensor.

Figure 3B:
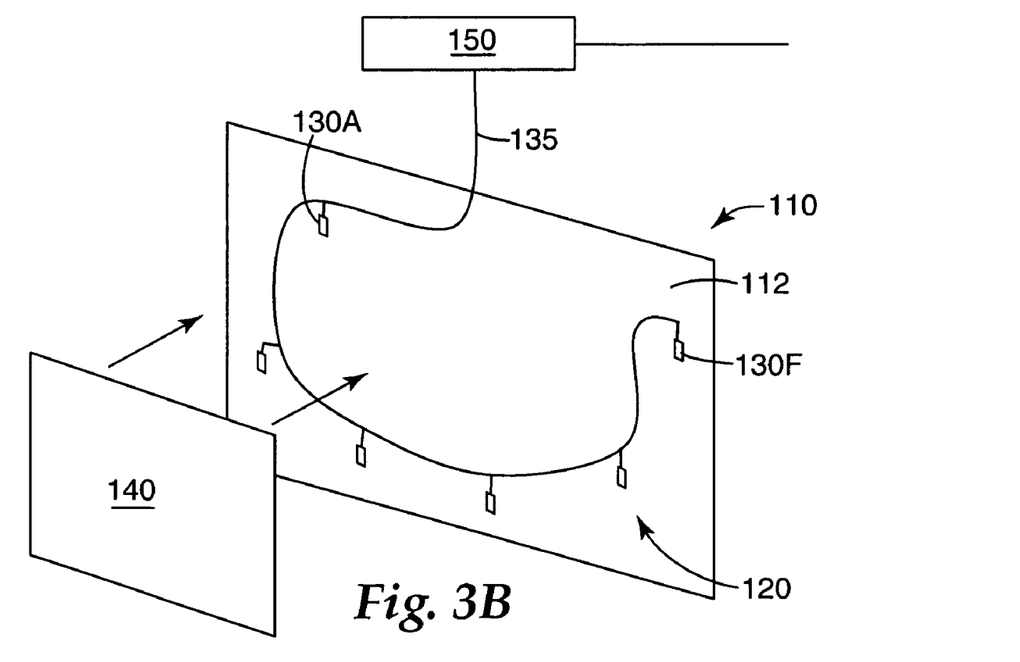
FIG. 3B is an exemplary detection system according to another alternative embodiment of the present invention.

In a further alternative, such as shown in FIG. 3B, sensor array 120 can comprise a plurality of individual sensors (in this example, sensors 130A-130F). Here, the individual sensors are coupled to the data acquisition circuit 150 in series. In this configuration, a detection scheme such as time domain reflectometry (TDR) can be used to detect corrosion at one or more particular locations. In this embodiment, the identity of the sensors can be determined by its location (delay) in the array. This configuration can allow the sensors to be designed as simple corrodible elements that provide an open when corrosion conditions are present. As would be understood by one of skill in the art given the present description, the coupling of sensors to the data acquisition circuit can be varied to include other arrangements, such as a combination of some of the elements of each of the arrangements shown in FIGS. 1, 3A, and 3B.

Figures 4A, 4B:
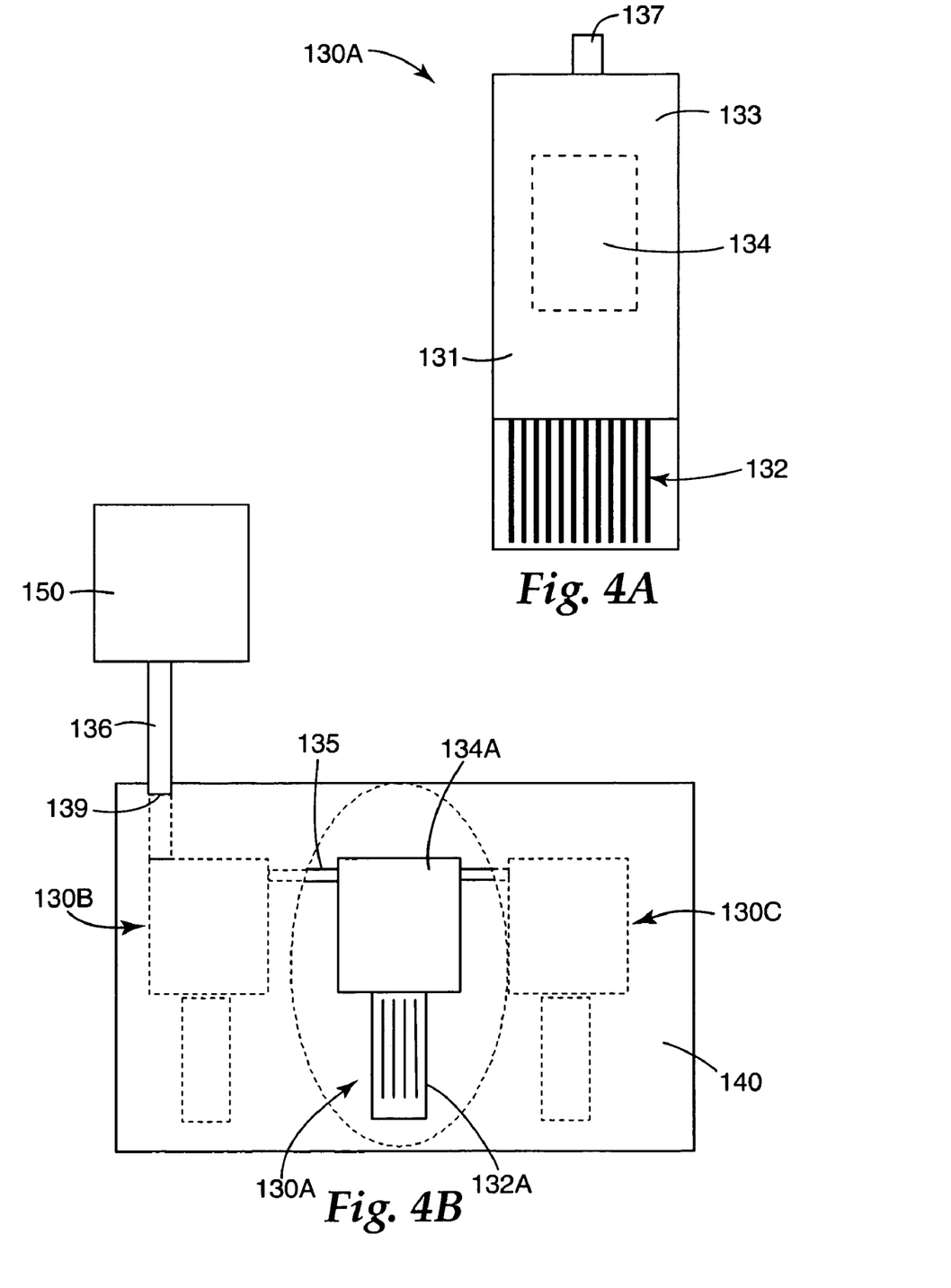
FIG. 4A is an exemplary sensor according to an embodiment of the present invention.
FIG. 4B is an exemplary detection system according to an alternative embodiment of the present invention.

The array of sensors of the exemplary detection system(s) can allow for spatial resolution of corrosion events. For accurate spatial resolution, the electrochemical data from each sensor can be differentiable from neighboring sensors. For example, as is shown in FIG. 4A, sensor 130A can include an embedded controller and/or identification (ID) chip 134. The embedded controller can receive data or readings from sensing portion 132 and communicate the information to the data acquisition circuit (e.g., circuit 150 from FIG. 1) via a data I/O port 137. In one exemplary embodiment, chip 134 can be configured in a similar manner to chip 138 described above.

Also, sensing portion 132 can include an electrode structure having interdigitated metal-based (e.g., gold, silver, copper) circuits, which can be used as anodes and cathodes for electrochemical/corrosion measurements, and can be formed on a flexible polyimide substrate. In addition, a portion of sensor 130A can be coated with its own protective overcoat 133 (e.g., covering the chip portion of the sensor, but leaving sensing portion 132 exposed to the structure 110 and coating 140).

In the example shown in FIG. 4B, a front view of sensors 130A, 130B, and 130C (through protective coating 140), the sensors can be serially connected via data lines 135, which are also disposed between the engineered structure and coating 140. Sensor 130A can include an interdigitated sensing portion 132A and a control chip portion 134A, such as described above. It is noted that the wire connections may need to extend through coating 140 at a location such as breakthrough area 139, where data line 136 communicates with data acquisition circuit 150. In a preferable aspect, area 139 is located in area portion of the structure that is not subject to as much exposure to deteriorating elements as other areas of the structure (e.g., near the top portion of a ballast tank).

Figure 5:
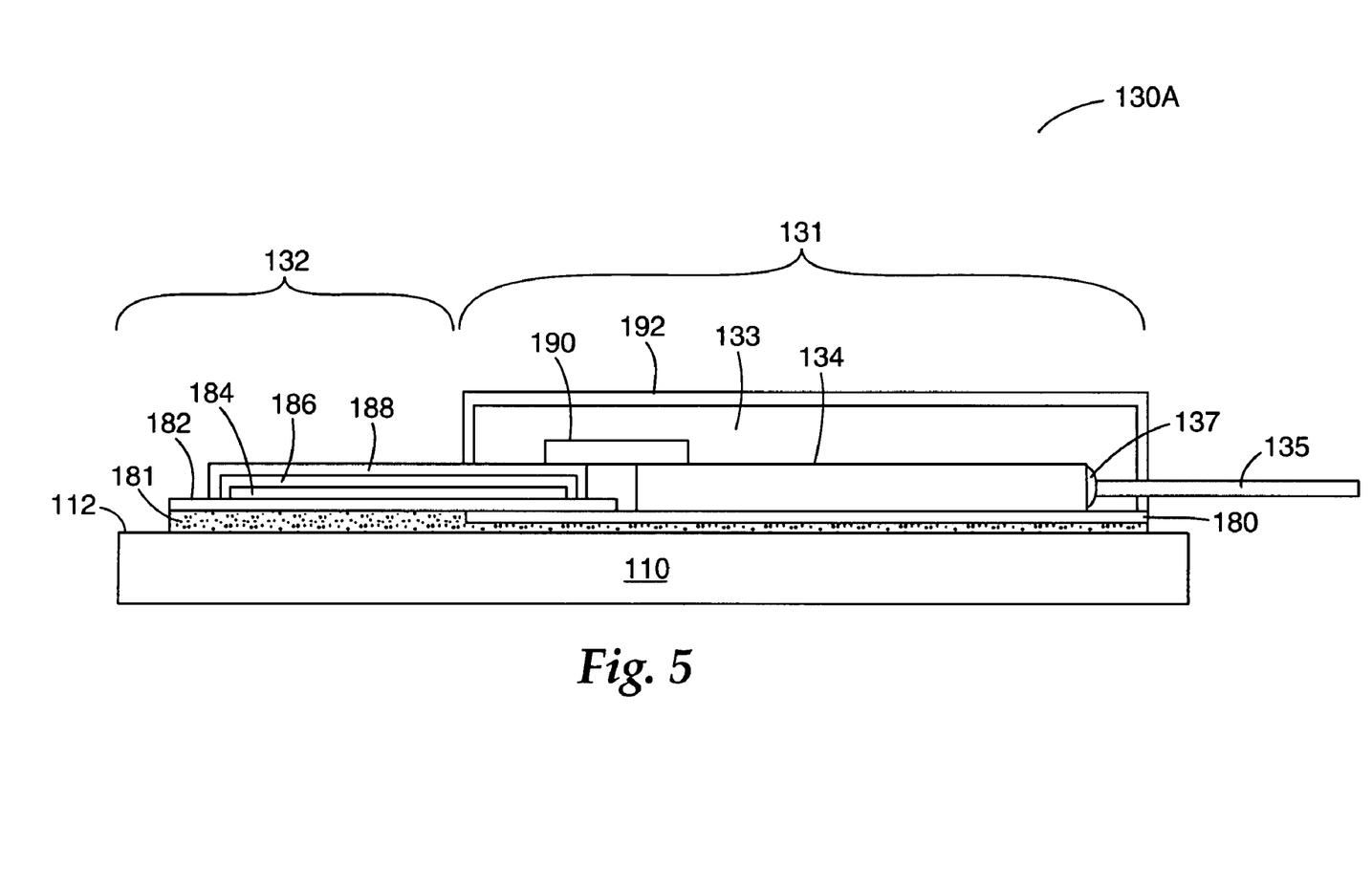
FIG. 5 is a cross section view of an exemplary sensor according to an embodiment of the present invention.

A cross section view of an exemplary sensor 130A is shown in further detail in FIG. 5. In this configuration, sensor 130A includes a sensing portion 132 and a control electronics portion 131 both disposed on a base material 180. Base material 180 can comprise a polymer-based material, e.g., a polyamide or alternatively, an acrylic material. Base material 180 can provide support for the control electronics portion and/or part of a hermetic seal with cap portion 192. Base material 180 and/or other portions of the sensor may be adhered to the surface 112 of engineered structure 110 by an adhesive 181 such as VHB adhesive available from 3M Company (St. Paul, Minn.). In a further alternative, all of or at least part of sensing portion 132 is not disposed on the base material 180.

In an exemplary embodiment, sensing portion 132 is formed on a thin, flexible substrate material, such as 3M's flexible circuit material, available under the trade name 3M™ Flex, from 3M Company, St. Paul, Minn. An exemplary article and process for making such a flexible circuit are described in U.S. Pat. No. 6,320,137, incorporated by reference in its entirety. By "flexible", it is meant that the sensor and (if applicable) substrate can be bent so that the sensing portion does not delaminate (e.g., the sensing portion can undergo 90 degree (or greater) bend at a very small radius of curvature, or even a sharp right angle or being creased, without losing its conductive qualities).

For example, the sensing portion can include a substrate 182, such as a polyimide material. The sensor electrode structure can be formed as a patterned multilayer material upon substrate 182 having, for example, a chrome tie layer 184, a copper (or other conductive) layer 186 disposed thereon, and a silver (or gold or other metal) layer 188 disposed on layer 186. Other multi-layer structures can be utilized, as would be apparent given the present description. Thus, a sensing portion 132 with an exemplary cathode-anode structure can provide the ability to measure a voltage drop between the cathode and anode, a current level between the cathode and anode, and/or measure impedance between the cathode and anode, at previously difficult-to-monitor locations.

In an alternative embodiment, the sensing portion 132 can be configured as an electrode formed of a chemical species that is sensitive to water, such as Al, Fe, or Zn. When the chemical species interacts with water, there will be a change in the measured impedance or resistance. Other corrosion sensitive species can also be utilized, as would be apparent to one of ordinary skill in the art given the present description.

The sensing portion 132 can be coupled to the control electronics portion 131 via a solder (or other material) link 190. The control electronics 131 can include a custom IC 134 that is coupled to I/O port 137, which provides data to and from sensor 130A via data line 135. Data line 135 (and/or data line 136 from FIG. 1) may include one or more conventional small gauge wires (e.g., 22 gauge) that are used to communicate data signals and/or power between electronic components. In one exemplary embodiment, parasitic power is provided to each of the sensors so the need for a separate third wire (to deliver power) is removed. Thin wires or cables may be preferable for traveling under and/or through coating 140.

A protective coating or encapsulant 133 can also be provided to protect the IC, circuit components and interconnects from exposure. Optionally, for further protection, a package cap material 192, such as a hard plastic, can provide an outer protective shell. The overall package thickness can be kept to about 100 µm to about 1000 µm.

Figure 6A:
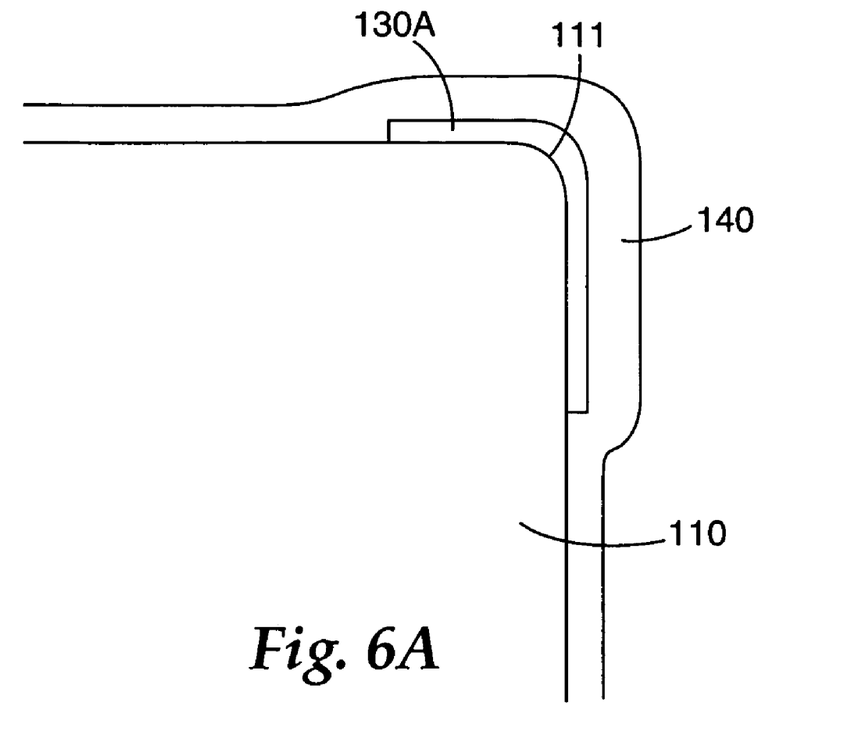
FIGS. 6A and 6B show alternative implementations of an exemplary sensor disposed on non-flat surfaces.
Figure 6B:
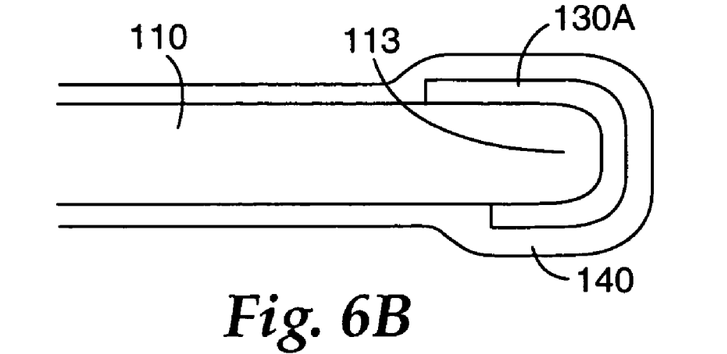
Figure 7:
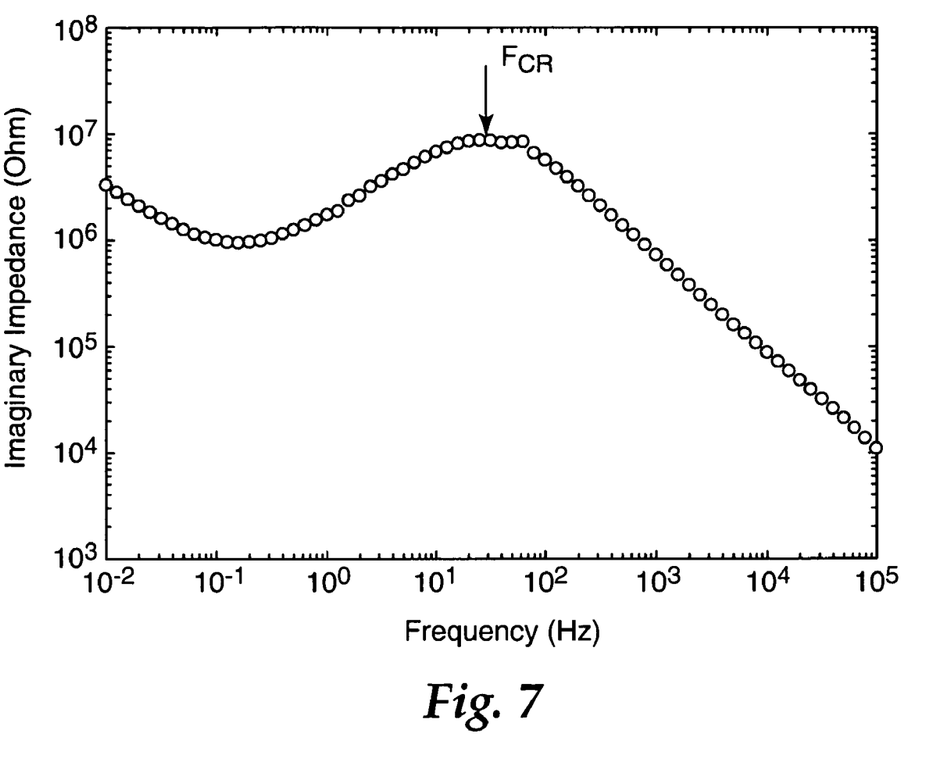
FIG. 7 shows a plot of imaginary impedance vs. frequency.

Using the above designs, exemplary embodiments of the detection system described herein can provide a non-disruptive, undercoating sensor, as shown in FIGS. 1 and 2. In addition, the sensors can be constructed on flexible, bendable substrates that allow a user to place sensors at critical areas of an engineered structure, such as non-flat surfaces (e.g., around bends and corners and other sharp-angled locations). These locations can be more susceptible to corrosion or other types of deteriorating events because protective coatings may not be evenly applied at corners and other sharp-angled locations. For example, as shown in FIGS. 6A and 6B, an exemplary sensor 130A can be disposed on a single corner surface 111 (FIG. 6A) or a multiple corner surface 113 (FIG. 6B) as might occur around the edge of an I-beam.

Referring back to FIG. 1, the sensors are in communication with a data acquisition (and control) circuit 150 via one or more data lines 135 and/or 136. This central unit 150 can be configured as a server or other computer-based device to communicate with sensor array 120, and alternatively, other sets of sensor arrays that are implemented to detect coating/structure health/deterioration in other structures (e.g., other ballast tanks, I-beams, pipes, etc.). For example, data acquisition circuit 150 can include an interface device, which communicates with the sensors or sensor groups, and a computer for data storage and display. Also, the data acquisition unit can be coupled to a separate display 152 to provide graphical data, such as real-time coating condition data, to a user.

As the data acquisition circuit 150 is a computer, server, or computer-based device, data collection, manipulation, analysis, and delivery can be provided via application-specific software programs loaded onto the circuit 150.

In some embodiments, by equipping each sensor with an onboard control chip having a unique ID and/or an analog to digital (A/D) converter, the detection system can allow electrochemical measurements to be made autonomously by the sensor, once external power is applied to the sensor. For example, the onboard A/D converter can send the measured voltage/current encoded with a unique ID to the data acquisition circuit.

In an example data collection routine, the data acquisition circuit 150 can initiate data collection by the sensors by sending activation power or other activation signal to the sensors of the array. The data acquisition circuit 150 can then search for all sensors and record and save all sensor addresses. A first sensor (or sensor group) can be read and a data request can be sent to that address. The specific sensor data from that address can be retrieved, decoded, analyzed, and/or stored in memory by data acquisition circuit 150.

For example, the IC chip (134, 138) can have two A/D converters, with the first A/D converter measuring the voltage across the sensing portion and the second A/D converter measuring the supply voltage provided by the data acquisition circuit. A ratio of the two voltages can be calculated by the data acquisition circuit based on the two measurements. This calculation can help compensate for variations in the supply voltage. This calculation can also act as a diagnostic for determining the presence of faulty electronics in the sensor array.

The data retrieval, decoding and storing can be repeated for all sensors or sensor groups. If a sensor indicates that a degradation of coating or structure has occurred, an alert can be provided to the user (e.g., in audible and/or visual format). Otherwise, data can be displayed (e.g., on display 152) upon user request. After a data acquisition run, the power to the sensors can be turned off. An automated process can be employed to activate data retrieval and analysis in a continual and/or periodic manner.

In another exemplary embodiment, detector system 100 can utilize a detection scheme as is illustrated by the following example. Using the exemplary interdigitated circuits formed on a flexible substrate as anodes and cathodes, it is possible to carry out electrochemical impedance spectroscopy and measure changes in the materials properties of the epoxy-type coatings during curing.

For example, a commercially available epoxy (3M product no. 2216 A/B, available from 3M Company, St. Paul, Minn.) was mixed, applied on a top surface of the sensor circuits. An electrochemical impedance spectroscopy (EIS) was carried out on the coating from 100 KHz to 0.01 Hz, with a 5 mV AC perturbation. An electrochemical potentiostat (model-PAR 273A), a frequency analyzer (model-Solartron 1260), and electrochemical software (model-Zplot) were used to conduct electrochemical impedance. Using EIS, the impedance response of the coating as a function of time was recorded.

Using a simple parallel capacitor (C) and resistor (R) circuit as a model of the coating AC response, a critical frequency ($F_{CR}$) can be defined based on the RC time-constant of the coating.

$$F_{CR} = -\frac{1}{2\pi RC}$$

From the EIS data the imaginary impedance component can be defined as:

$$Z_{IM} = -\frac{1}{\omega^\alpha C}\sin\left(\alpha\frac{\pi}{2}\right)$$

where $Z_{IM}$=imaginary impedance/resistance, $\omega$=radial frequency, $\alpha$=constant phase element constant, and C=capacitance. Assuming that $\alpha$ approaches 1 for an ideal capacitance behavior and the capacitance can be treated as a parallel plate:

$$C = \frac{A\varepsilon\varepsilon_o}{d}$$

where d=thickness of the dielectric, $\varepsilon$=dielectric coefficient, and $\varepsilon_0$=permittivity constant. The R value can be obtained from the real portion of the EIS data. The coating resistance is then defined as:

$$R = \frac{\rho d}{A},$$

where A=area of the dielectric, and $\rho$=resistivity, in ohms-cm. Simple substitution leads to:

$$F_{CR} = \frac{1}{2\pi\rho\varepsilon\varepsilon_o}.$$

Figure 8A:
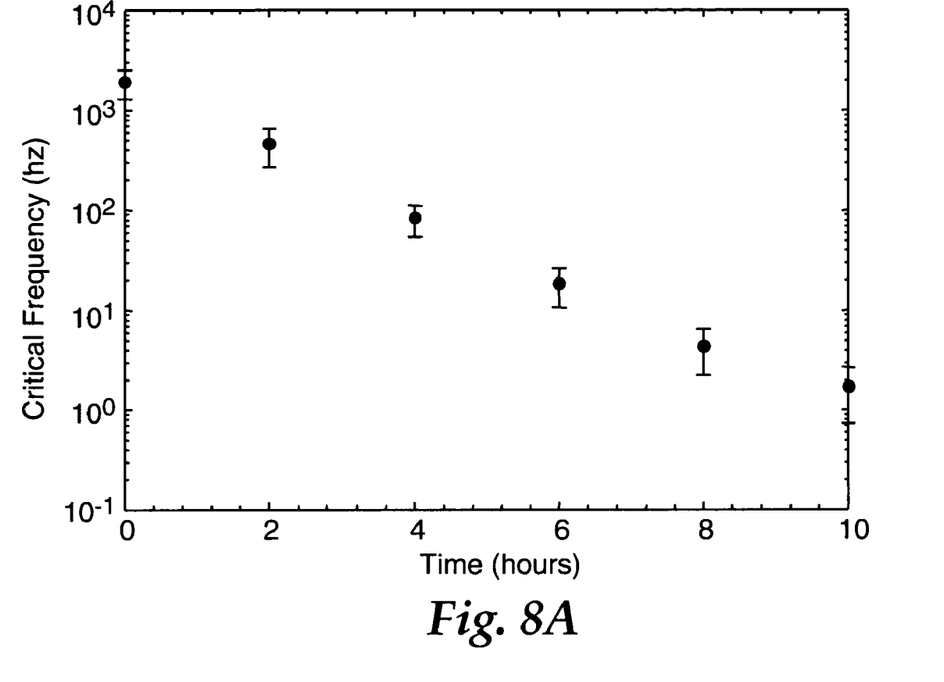
FIGS. 8A and B show plots of critical frequency vs. time over different time scales for an exemplary coating.

As defined above, the frequency ($F_{CR}$) is dependent on the material properties of the coating, not the geometry. The critical frequency, defined as the maxima of the imaginary impedance, is shown in FIG. 8A. This critical frequency can be used to monitor changes in the actual coating, both to watch the cure of the epoxy and later to follow the degradation of the coating.

Figure 8B:
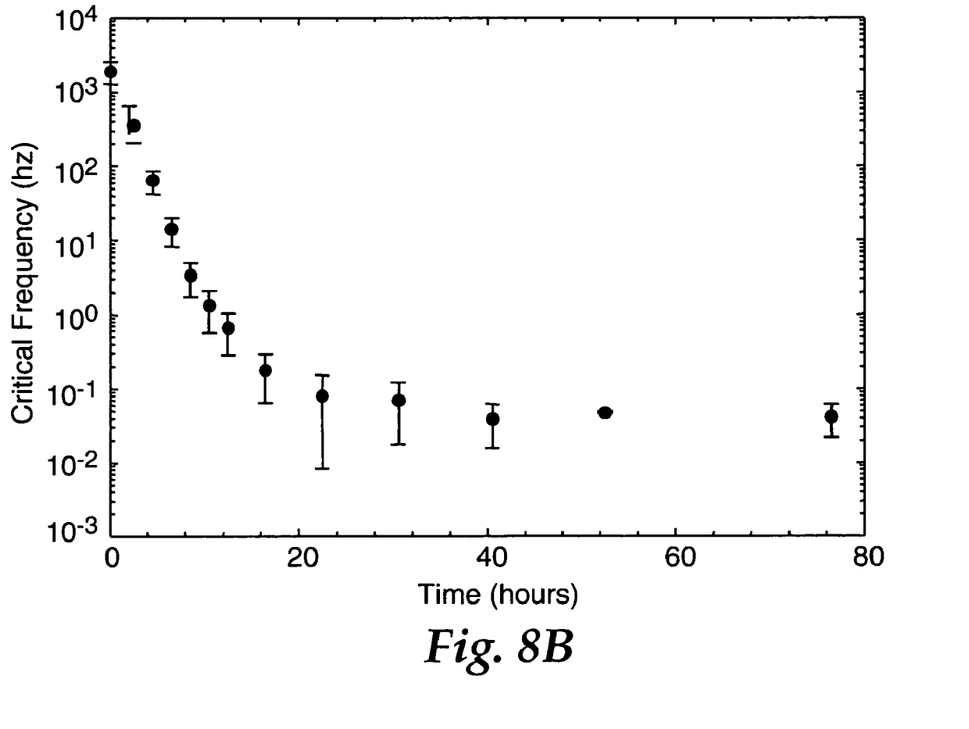

Additionally, plots showing values for $F_{CR}$ vs. time (for two different time scales), from the application of the sample epoxy on the sensor, are shown in FIGS. 8A and B. The changing critical frequency in FIG. 8A indicates that the measured system is not stable during cure, as the decreasing critical frequency indicates an increasing resistivity and/or increasing dielectric coefficient, both of which can be expected for the curing of an epoxy coating. As seen in FIG. 8B, after a recommended curing time for the sample epoxy (e.g., for this sample, about 24 hours), the $F_{CR}$ is stable and the critical frequency reaches a steady state. This critical frequency value then becomes a baseline to compare longer term coating degradations against.

Using the interdigitated circuits as electrodes under the coating (similar to the designs described above), electrochemical impedance spectroscopy allows measurement of the changes in material properties of the epoxy-type coatings due to exposure to ASTM D665 (i.e., synthetic sea water). 3M flexible circuits with 3M epoxy 2216 A/B, or a MIL-Spec 24441 coating (available from NCP Coatings, Inc. Niles, Mich.) were immersed in ASTM D665 seawater at room temperature. Electrochemical impedance spectroscopy (EIS) was carried out from 100 KHz to 0.01 Hz, with a 100 mV AC perturbation at 0 V. Electrochemical potentiostat (PAR 273A), frequency analyzer (Solartron 1260), and electrochemical software (Zplot) were used to conduct electrochemical impedance.

Figure 9:
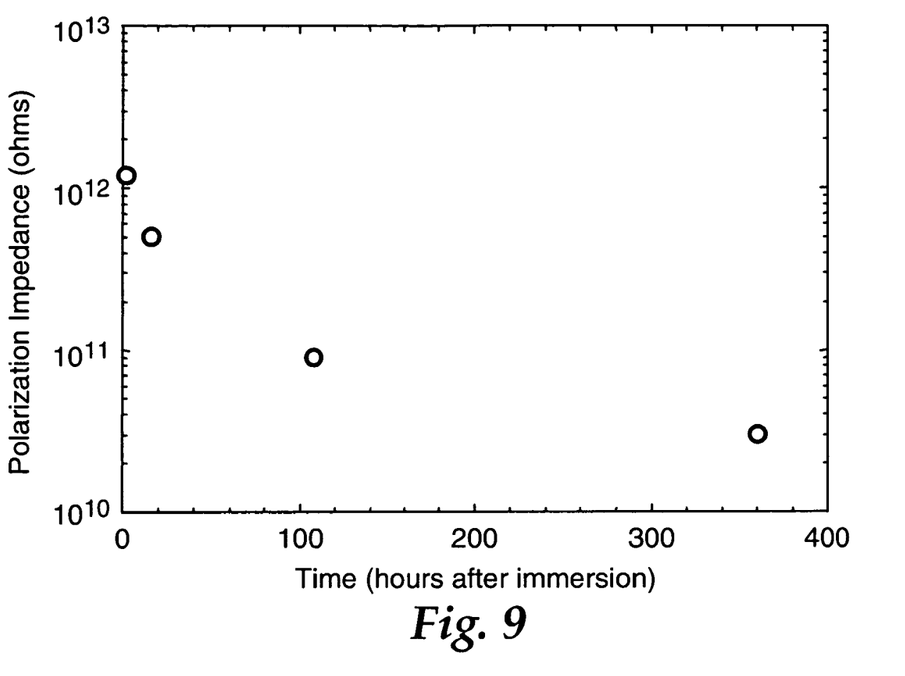
FIG. 9 shows a plot of the coating impedance as a function of time upon exposure to salt water.

The electrochemical impedance data of a corrosion system can be represented by an equivalent electronic circuit containing frequency dependent elements such capacitors, inductors, and constant phase elements. Using these elements, the data can be modeled and the materials properties of the electrodes or materials in contact with the electrodes can be determined. As shown in FIG. 9, for the MIL-24441 paint coating, the electrochemical impedance detected by the embeddable sensor decreases over time, most likely due to the penetration of moisture and/or ionic species into the sample coating.

Figure 10:
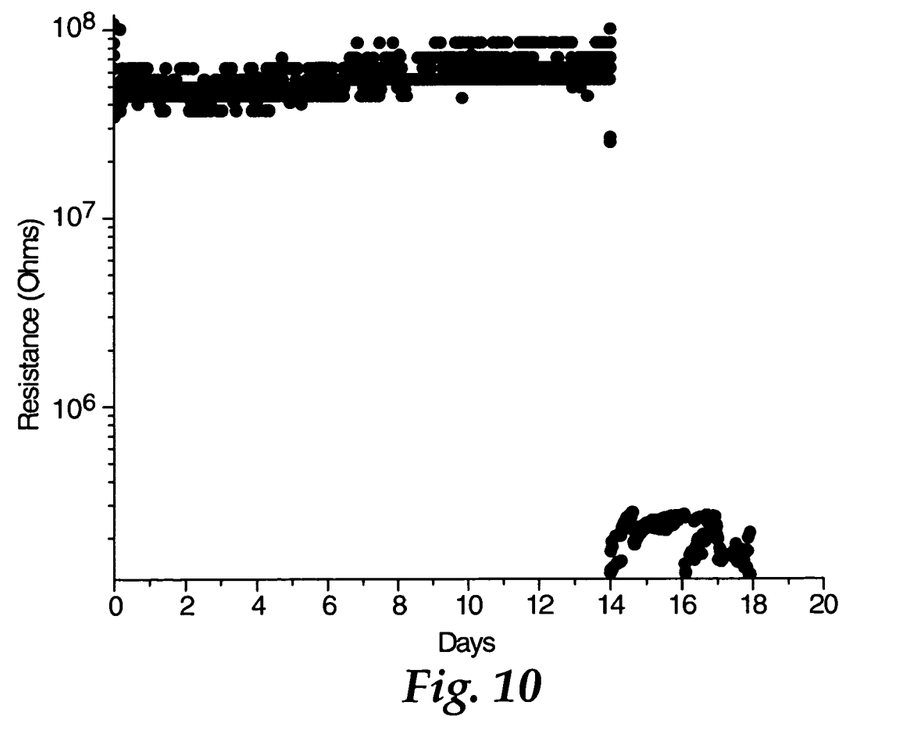
FIG. 10 shows a plot of the measured impedance of an immersed example coating as a function of time.

In another experiment, as shown in FIG. 10, the measured impedance for a Mil-Spec 24441 type coating that is immersed in ASTM665 Seawater is displayed as a function of time. A coating shows little change in the impedance over the first 14 days of the test. On day 14, a 1 mm×1 mm defect was purposely introduced to the sample. Following the damaging of the coating, the coating shows a significant drop in impedance, due to exposure to excess moisture and ion uptake. The sensor detected this severe change.

Thus, according to the above exemplary embodiments, embeddable corrosion sensors can be provided to detect moisture ingress, the ingress of species such as chlorides and other anionic species, coating curing, coating health, and structural health. As such sensors can be formed on flexible substrates, more location-specific real-time measurements can be provided to the user. Also, such thin circuits (e.g., ~0.001"thick) can be placed between a protective coating and the structure without adversely affecting the coating condition. Also, the data acquisition system can provide real time measurement of corrosion-related events. Such a corrosion sensor can help reduce the direct and indirect cost of corrosion related damage.

Various modifications, equivalent processes, as well as numerous structures to which the present invention may be applicable will be readily apparent to those of skill in the art to which the present invention is directed upon review of the present specification.

What is claimed is:

1. A detection system for monitoring a physical condition of an engineered structure, comprising:
    an array of sensors disposable in a predetermined pattern on the engineered structure and disposable between a surface of the engineered structure and a protective coating substantially covering said surface; and
    a data acquisition system in communication with the array of sensors for retrieving data from said sensors, the array of sensors providing data corresponding to at least one of a degree of cure of the protective coating and a corrosion rate of the engineered structure at each of the sensors, wherein at least one sensor of the array comprises:
    a sensing portion configured to detect at least one of an impedance, current, and voltage, said sensing portion disposed on a flexible substrate, and
    a control electronics portion including a unique address,
    wherein the sensing portion comprises a conductive element patterned as at least two electrodes on the flexible substrate, and wherein the control electronics portion includes voltage and current control electronics.

2. The detection system of claim 1, wherein the sensing portion is disposable on a non-flat surface of the engineered structure.

3. The detection system of claim 1, wherein at least a portion of the plurality of sensors of the sensor array are coupled serially.

4. The detection system of claim 1, wherein at least a portion of the plurality of sensors of the sensor array are coupled in parallel.

5. The detection system of claim 1, wherein the array of sensors are coupled to the data acquisition system via a data line.

6. The detection system of claim 1, wherein the engineered structure comprises at least one of a metallic, composite, ceramic, and fiberglass material.

7. A method of detecting physical conditions in an engineered structure:
    providing a data acquisition circuit that provides an activation signal initiating data collection from an array of sensors, each of the sensors including a sensing portion, the array of sensors being disposed between a surface of the engineered structure and a protective coating substantially covering said surface;
    searching for at least a portion of the array of sensors and recording and saving all searched sensor addresses;
    retrieving data from a first sensor of the searched sensors;
    analyzing the retrieved data;
    storing the analyzed data; and
    displaying the stored data upon request, wherein the analyzed data corresponding to at least one of a degree of cure of the protective coating and a corrosion rate of the engineered structure at each of the sensors, wherein the activation signal provides power to each of the sensors of the array.

8. The detection method of claim 7, further comprising repeating the retrieval, analyzing, and storing steps for a second sensor of the array.

9. The detection method of claim 7, further comprising providing an alert when the sensor indicates that one of a degradation of the coating and a degradation of the structure has occurred.

10. The detection method of claim 7, further comprising turning off the power to the sensors.

11. The detection method of claim 7, comprising detecting a first voltage across a sensing portion of the first sensor and detecting a second voltage at the first sensor wherein the second voltage corresponds to a voltage supplied by the data acquisition circuit, and calculating a ratio of the first voltage and a second voltage.

* * * * *